US006485763B1

(12) United States Patent
Jampen

(10) Patent No.: US 6,485,763 B1
(45) Date of Patent: Nov. 26, 2002

(54) SHELF-STABLE, SPREADABLE MAPLE SYRUP COMPOSITION

(75) Inventor: Stephan Jampen, Guelph (CA)

(73) Assignee: 2002872 Ontario Limited Inc., Toronto (CA)

( * ) Notice: Subject to any disclaimer, the term of this patent is extended or adjusted under 35 U.S.C. 154(b) by 0 days.

(21) Appl. No.: 09/858,602

(22) Filed: May 17, 2001

(51) Int. Cl.$^7$ .............................. C13K 3/00; C13F 3/00
(52) U.S. Cl. ......................................... 426/48; 426/655
(58) Field of Search ........................... 426/48, 52, 322, 426/638, 589, 658, 655

(56) References Cited

U.S. PATENT DOCUMENTS

| | | | |
|---|---|---|---|
| 3,615,701 A | 10/1971 | Goss | 99/142 |
| 3,878,306 A | 4/1975 | Garstick | 426/658 |
| 4,006,032 A | 2/1977 | Hills | 127/46 |
| 4,159,210 A * | 6/1979 | Chen et al. | 127/29 |
| 4,938,989 A | 7/1990 | Steeves et al. | 426/658 |
| 5,049,199 A | 9/1991 | Capen | 127/9 |
| 5,389,209 A | 2/1995 | Paquette | 203/14 |
| 5,876,506 A * | 3/1999 | Cherukuri et al. | 127/30 |

OTHER PUBLICATIONS

Woodward et al., "Enzymatic Conversion of Sucrose to Hydrogen", Biotech. Prog., 14(6): 897–902, Nov. 1998.*

H.A. Edson, et al., Vermont Agricultural Experiment Station, Bulletin No. 167, University of Vermont and State Agricultural College, Burlington, VT, Jun. 1912, pp. 324–605.

The Ohio State University Bulletin, North American Maple Syrup Producers Manual, Bulletin 856, Chapter 7—Maple Syrup Production, Increasing Evaporation Efficiency, through Chapter 9—Other Maple Produces., Dec. 1998.

The Ohio State University Bulletin, North American Maple Syrup Producers Manual, Bulletin 856, Appendix 2—Maple Chemistry and Quality., Dec. 1998.

J.F. Steffe, Rheological Methods in Food Process Engineering, second edition, Freeman Press, East Lansing, MI, pp. 26, 82 and 367, Jan. 1996.

AOAC Official Method 977.20, Separation of Sugars in Honey, Liquid Chromatographic Method, Jan. 1998.

Hayward, et al., Some Factors Causing Dark–Colored Maple Sirup, New York State Agricultural Experiment Station, Bulletin No. 718, Mar. 1946.

* cited by examiner

*Primary Examiner*—Keith Hendricks
(74) *Attorney, Agent, or Firm*—Fitzpatrick, Cella, Harper & Scinto

(57) ABSTRACT

A method for producing a shelf stable, spreadable high viscosity maple syrup product is provided, which comprises adding a sucrose-cleaving enzyme to maple syrup and incubating the resulting solution. Also provided is a shelf stable, spreadable maple syrup product with a consistency similar to that of honey, which may be used as a spread, or sweetener or a topping. It is also suitable for use in pure maple-based products.

28 Claims, 1 Drawing Sheet

SHELF-STABLE, SPREADABLE MAPLE SYRUP COMPOSITION

FIELD OF THE INVENTION

Figure 1:
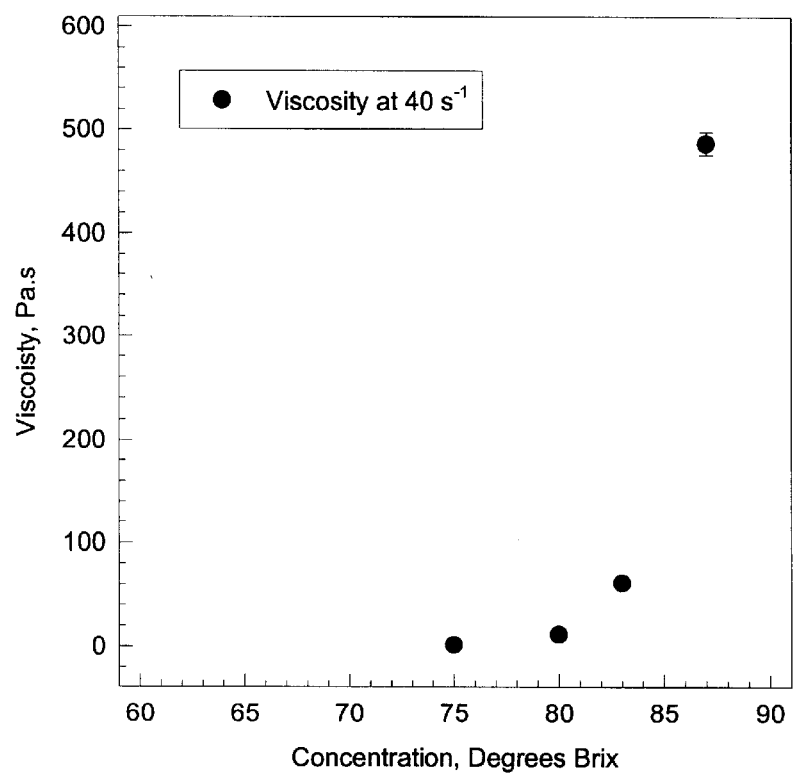

The present invention relates to a spreadable, shelf stable maple syrup product.

BACKGROUND OF THE INVENTION

The sap of maple trees forms the basis of maple syrup products, including maple syrup, maple sugar and maple confection products. Maple syrup is obtained by the concentration of maple sap, a low solids (low sugar) solution obtained from the maple tree, to a solids content of 66 percent (66 degrees Brix). The production of maple syrup and related products is highly regulated in Canada and the United States, such that all additives are prohibited. As a result, maple producers cannot simply use additives such as stabilizers if they wish to label their product as a "pure maple product" or as "pure maple syrup".

To produce maple syrup, the sap from maple tree is concentrated to 66 degrees Brix (at 68 degrees Fahrenheit; 20 degrees Celsius) to be considered as "pure maple syrup" by U.S. and Canadian law. About 40 liters of maple sap are needed to make 1 liter of maple syrup. During the evaporation process, the sap is heated which induces chemical changes that give maple syrup its characteristic color and flavor. These chemical changes include non-enzymatic browning and caramelization reactions (Edson, 1910; Hayward and Pederson, 1946).

Concentration can be achieved through simple boiling in an open kettle or using more advanced evaporation techniques such as vacuum pan evaporators and rising film or falling film evaporators. Various other methods are known for concentrating maple sap. For example, U.S. Pat. No. 5,389,209 to Paquette discloses a method of boiling the sap under normal pressure, then heating the sap to below boiling temperature and using an air circulating column to further evaporate the water. Reverse osmosis can be used to pre-concentrate the sap to about 20 –25 degrees Brix. An alternate concentration step, which involves the addition of heat, must be used to complete the concentration to 66 degrees Brix such that the characteristic maple flavor is created (North American Maple Producers Manual, Bulletin 856, chapter 7).

Concentrating to a higher level (over 67.5 degrees Brix) will result in crystallization of the sucrose, the main sugar found in maple sap, within the container while in storage. Conversely, a maple syrup of lower Brix (under 64.5 degrees Brix) would spoil (ferment) while in storage. Crystallization occurs because the main sugar in maple syrup is sucrose (90–100 percent), with the rest glucose being (0 to 10 percent) (North American Maple Syrup Producers Manual, Bulletin 856, Appendix 2).

It is the crystallization behavior of maple syrup at higher concentration that allows for the production of other maple products such as maple sugar. These products are obtained by concentrating maple syrup past 66 degrees Brix. At these elevated Brix levels, a supersaturated sucrose solution is made. Therefore, if this solution is cooled, crystallization will occur. Depending on the rate of cooling and/or whether agitation is present during the cooling process, characteristic maple products are obtained. Slow cooling without agitation results in crystals that are very large, often termed "rock candy". More rapid cooling, but again without agitation, will result in smaller crystals but the product has a very gritty mouthfeel. When a highly supersaturated maple syrup solution (85 to 90 degrees Brix) is cooled very rapidly, a non-crystalline glass-like solid is obtained (North American Maple Syrup Producers Manual, Bulletin 856, chapter 9).

Conversely, if a supersaturated (84 to 85 degrees Brix; or 12 to 13 degrees Celsius above the boiling point of water) maple syrup solution is cooled rapidly with high-speed agitation, very small crystals are obtained with the resultant product being paste-like in consistency and is spreadable. This product is known as maple butter or maple cream.

Crystallization of the sugars found in maple syrup is random and occurs spontaneously at higher Brix levels. Because the crystallization behavior of concentrated maple sap is difficult to control, only a select few products have been developed. Additionally, at a concentration of 66 degrees Brix, maple syrup may be too runny (thin) to be used in an application such as a honey like spread. Currently, there is no natural or pure maple product which has the consistency and/or appearance similar to that of liquid honey.

Liquid honey is a transparent high viscosity 3.9 Pascal seconds sugar syrup with a moisture content of 17 to 19 percent (81 to 83 degrees Brix solids) (Rheological Methods in Food Process Engineering, Steffe, J. F. 1996, pp 82, 26 and 367). This material remains in a liquid state, without crystallization for extended periods of time. The main sugar components in honey are the monosaccharides glucose and fructose. These sugars are present in maple syrup in small amounts.

As previously described, a more viscous solution similar to that of liquid honey, having a unique maple flavor, is attainable by further concentrating maple syrup to a higher Brix level (81 to 82 degrees Brix for example). However, crystallization occurs rapidly such that the clear viscous solution would not be preserved. This occurs because the main sugar in maple syrup is the disaccharide sucrose, which crystallizes much more readily than glucose and fructose.

Pure glucose and fructose blends are available commercially and are known as invert sugars. It is known to use invert sugar (glucose/fructose) when making artificial maple products. It is also known that invert sugar tends to retard crystallization in maple products. However, simply adding invert sugar can lead to loss of natural maple flavor. Additionally, the resultant maple product may no longer be labeled as pure under the Canadian and U.S. legal standards.

Invert sugars have also been used in making imitation maple syrup or syrup substitutes. U.S. Pat. No. 3,878,306 to Garstick discloses an imitation maple syrup made from various sugars and artificial flavorings. U.S. Pat. No. 4,938,989 to Steeves and McKelvey provides a maple syrup substitute which contains maple syrup, maple flavor, fructose and glucose and white sugar. Again, these products could not be considered pure maple products.

It is known in the art that sucrose can be cleaved into its constituent sugars, glucose and fructose by use of an acid such as L-tartaric acid (cream of tartar). However, the use of organic acids leads to products that have very poor flavor profiles and unacceptable appearances. A further challenge is that the acid would have to be removed, after it has cleaved the sucrose. This step would also remove important flavor components.

The difficulty in making stable high viscosity maple syrups extends to other maple products. For example, maple butter (also called maple cream or maple spread) separates into two layers if not stored at temperatures below 0 degrees Celsius or 32 degrees Fahrenheit. A dilute syrup layer forms on top and a solid crystalline mass forms underneath. Maple butter is made by heating maple syrup to 11 to 13 degrees Celsius above the boiling point of water (83 to 85 degrees Brix), and cooling rapidly while stirring. It is known that a small amount of invert sugar present in the syrup results in a finer texture. However, according to the North American Maple Syrup Products Manual, syrup with greater than 4 percent of invert sugar is not considered suitable. It is known that when maple syrup containing more than 4 percent invert sugar is used to make maple butter, the spreadability is poor and the product separates more rapidly.

Accordingly, there is a need for a shelf stable, spreadable, non-crystalline maple syrup product with the consistency of liquid honey.

SUMMARY OF THE INVENTION

An object of the present invention is to provide a shelf stable, spreadable, non-crystalline maple syrup composition with a consistency similar to that of liquid honey. The composition is preferably transparent or translucent.

Another object of the present invention is to provide a spreadable, shelf stable maple syrup product having a Brix measurement of between about 75 and about 90 degrees Brix. Preferably, the Brix measurement is between about 77 and about 87 degrees, with the most preferred range being between about 82 to about 85 degrees.

Another object of the invention is to provide a method for producing a shelf stable maple syrup composition with a consistency similar to that of liquid honey comprising treating maple syrup with a sucrose-cleaving enzyme. Preferably, the sucrose-cleaving enzyme is invertase. Preferably, the method includes the additional step of concentration of the maple syrup to between about 75 and about 90 degrees Brix.

According to an aspect of the invention there is provided a method for producing a stable high viscosity maple syrup product comprising adding a sucrose cleaving enzyme to maple syrup and incubating the resulting maple syrup solution.

According to another aspect of the invention there is provided a shelf stable, spreadable maple syrup composition having a Brix measurement of between about 75 and about 90 degrees.

According to a further aspect of the invention there is provided the method of using the shelf stable, spreadable maple syrup composition as a spread, sweetener or in other food products such as ice cream or other desserts.

DETAILED DESCRIPTION OF THE DRAWINGS

FIG. 1 is a graph showing the viscosity profile of a 55:45 enzyme treated to non-enzyme treated blend of maple syrup at various concentrations.

DETAILED DESCRIPTION OF THE INVENTION

The present invention provides a spreadable maple syrup composition which is shelf stable, having a viscosity similar to that of honey. The maple syrup composition may be used in a similar manner as honey: as a spread on bread products, topping for other food products such as ice cream or other desserts, or as a sweetener in home cooking and/or in commercial food products. It is also suitable for use in pure maple-based products.

"Maple syrup" when used herein means the concentrated sap of trees of the botanical genus Acer.

"Maple butter" when used herein means the creamy smooth textured product obtained by the rapid cooling of a supersaturated maple syrup solution under high amounts of agitation. Maple butter is also known as maple cream or maple spread.

"Shelf stable" when used herein means that the maple syrup composition is substantially free from crystallization for a period of at least 3 months.

"Brix" when used herein describes a measure of what the percentage of sugar could be if the density of the solution were due only to dissolved sugar. In the case of maple syrup, the Brix value, as measured by refractometer or hydrometer, essentially equals the amount of sugar present because most (about 98 %) of the solids are sugars.

"About" when used herein in relation to Brix measurement, means ±3 % or ±2 units of measure.

"Spreadable" when used herein means having a consistency similar to that of liquid honey.

A "sucrose-cleaving enzyme" is a hydrolysis enzyme which preferentially cleaves the beta-D-fructofuranoside linkage between the glucose and fructose molecules that make up sucrose.

To make the high viscosity maple syrup of the present invention, any grade of maple syrup may be used as the starting material. Preferably, the maple syrup is high grade. The maple syrup is placed in a sanitary vessel such as a sterile agitated incubation tank and may optionally be diluted in order to optimize reaction conditions. Preferably, the maple syrup is diluted using sterile deionized water to a final Brix content of 55 degrees. Alternatively, maple sap which has been concentrated to a final sugar Brix content of only 55 degrees may be used in place of maple syrup.

An enzyme which cleaves sucrose into glucose and fructose is added to the maple syrup. Preferably an invertase enzyme is used. There are two main groups of invertase enzymes: 1) alpha-glucosidases which are also known as maltase, glucoinvertase, glucosidosucrase, maltase-glucoamylase, lysosomal alpha glucosidase, and acid maltase and 2) beta fructofuranosidases which are also known as invertase, saccharase and beta-fructosidase. Invertase is available commercially from Sigma Chemicals (Grade V: Practical from baker's yeast) and is used in the baking industry to control the amount of surface browning in bread and cookies. Invertase is added in the amount of 0.05 % of the final weight of the diluted mixture. Invertase is sucrose specific and self-terminating in that once all of the substrate sucrose is cleaved, nothing else will be hydrolyzed.

The solution may be adjusted to the optimal pH for invertase pH 4.6 through known pH adjustment methods. Preferably, to maximize the natural maple flavor, the pH is not adjusted and the reaction still proceeds at the natural pH of maple syrup (pH 6.8). The time necessary to complete the hydrolysis of sucrose to glucose and fructose increases with increasing pH. At pH 6.8, complete conversion takes approximately 7 days.

The incubation temperature is preferably between 15 and 35 degrees Celsius and most preferably, the incubation should take place at room temperature (20 –23 degrees Celsius) under continuous gentle agitation. Because of the low Brix, sanitary practices should be used when sampling and in further processing due to the potential for microbial growth.

The cleavage of sucrose to glucose and fructose can be monitored using various known methods. The preferred method is monitoring the optical rotation of the sugars. As the hydrolysis progresses, the muta-rotation decreases, and is negative when complete. A second method encompasses monitoring the hydrolysis using HPL techniques methods (AOAC Official Method 977.20, Separation of Sugars in Honey). Glucose, fructose and sucrose can be separated by a carbohydrate column (Waters Inc., carbohydrate analysis column, part no. 84038) using a mobile phase of 83:17 acetonitrile: water. With corresponding standards, the three sugars can be identified and quantified. Hydrolysis is deemed complete after negligible amounts of sucrose are detectable.

Once the reaction is complete, preferably, the invertase enzyme is removed from the mixture. The advantages of removing the enzyme from the syrup are to remove the visible haze and to remove the protein source which could initiate the Maillard browning reaction upon heating in the evaporation step. The Maillard reaction potentially creates bitter flavors, which would be objectionable in this product.

The enzyme can be removed by known means, including precipitation, hydrolysis and filtration. Preferably, the invertase is removed by filtration through a filter of pore size of less than 1 mm.

It is also within the scope of this invention that the enzyme be immobilized onto a resin bead that is then placed into a reaction column. The maple syrup is flushed through the column on a continuous basis, allowing the reaction to occur as the maple syrup passes over the resin beads onto which the enzyme had been attached. In such a case, the enzyme does not have to be removed through alternate means such as filtration as it remains bound to the resin beads in the column.

Once the enzyme is removed, the syrup can be concentrated to any concentration, depending on the viscosity that is desired in the product. It is preferably concentrated to between 75 and 90 degrees Brix, and most preferably to between 82 and 85 degrees Brix. This may be accomplished using known methods such as heating in an open kettle, vacuum pan evaporators and rising film or falling film evaporators, or reverse osmosis. Concentration of the syrup is most preferably accomplished by heating the syrup to a high temperature for short periods of time and flashing off the appropriate quantities of water to reach the desired Brix level. Low temperatures for longer periods of time with vacuum can also be used. Low temperature long time concentration is best carried out between 50 and 80 degrees Celsius, more preferably from 50 to 65 degrees Celsius and most preferably at 65 degrees Celsius and under vacuum (about 0.8 bar). The high viscosity syrup product produced in this manner may then be used by a consumer after the usual packaging steps, or it may be packaged and provided to the consumer.

To further improve the flavor profile, the dilute enzyme treated syrup is preferably blended with untreated maple syrup of any grade prior to concentration.

Optimum blends are 50:50, 55:45 and 60:40 (enzyme treated to non-enzyme treated syrup). The blended syrup can then be concentrated as described above. The maple flavor profile can be tailored to suit the retail climate by using different grades of maple syrup with varying flavor profiles in the incubation step and the blending step. The color of the final product can be controlled in a similar manner.

The present invention is described in more detail by reference to the following specific examples which are not to be construed as limiting.

EXAMPLE 1

Addition of Invert Sugar to Maple Syrup

The first stabilization technique evaluated was simple addition of invert sugar (glucose and fructose) to maple syrup and then concentrating to 82 degrees Brix on a hot plate. Four different levels of invert sugar were added: 1, 6, 10, and 20 percent. Crystallization was evident in all samples within three weeks of storage at room temperature. Interestingly, the more invert sugar added, the longer the time before crystallization was evident. However, with increasing invert sugar content, the maple flavour decreased substantially. The type of invert sugars was also evaluated. Three different invert sugars, solid invert, medium invert and high fructose corn syrup, were added at 20 percent of the total volume to 66 degrees Brix maple syrup and concentrated to 80 to 82 degrees Brix. Crystallization appeared in each of the samples within about three weeks.

EXAMPLE 2

Addition of Cream of Tartar to Maple Syrup

Cream of tartar (L-Tartaric Acid, Sigma Chemicals, Oakville, ON, Canada.) is an accepted way of converting sucrose to glucose and fructose (North American Maple Producers Manual s.7). Three levels of tartaric acid were evaluated: 0.02, 0.08 and 0.10 percent. Tartaric acid was added to the 66 degrees Brix maple syrup. The solution was heated to boiling, as it was thought that the heat added in concentrating the syrup to 80 –82 degrees Brix was thought to be sufficient to cleave a portion of the sucrose to glucose and fructose. However, the resultant samples were very bitter in taste and had a distinct hazy appearance. All samples also crystallized after a two-day period at room temperature.

EXAMPLE 3

Enzymatic Cleavage of Sucrose to Glucose and Fructose with pH Adjustment

The enzyme invertase (Sigma Chemicals, Oakville ON, Canada) was used to cleave sucrose to glucose and fructose. The optimal pH for this specific invertase enzyme is 4.5. However, the natural pH of maple syrup is 6.8. In the first trial, 1 kg of maple syrup was placed in a sterile container. The pH of the maple syrup was adjusted to 5.0 using tartaric acid, closer to the optimal pH of the enzyme. To this, enzyme was added (1 g enzyme per 500 g syrup). In order to assist in the dispersion of the enzyme, the maple syrup was diluted to 55 degrees Brix using sterile deionized water. The solution was divided into two portions with one portion incubated at room temperature (22 to 23 degrees Celsius) and the other was incubated at 33 degrees Celsius. After a 6 day incubation period the sucrose, glucose and fructose content was determined using HPLC methods (AOAC Official Method 977.20, Separation of Sugars in Honey). At both temperatures, all of the sucrose had been converted to glucose and fructose. A filtration step was then carried out to remove the enzyme (Whatman No. 42, Slow, Fine Crystalline Material; Fisher Canada, Napean, ON, Canada). The syrup was placed in a beaker atop a hot plate and heated to boiling. Concentration of this syrup to 82 Brix resulted in a product that was substantially free of crystals, and was shelf stable at room temperature for at least 2 months.

EXAMPLE 4

Enzymatic Cleavage of Sucrose to Glucose and Fructose without pH Adjustment

In an effort to reduce the effect of pH adjustment on the flavor of the product, the activity of the enzyme invertase was evaluated in maple syrup at the normal pH of maple syrup (pH 6.8) as described in Example 3. The incubation was carried out at room temperature, and allowed to proceed for 11 days. HPLC analysis of the sample showed that all of the sucrose had been converted to glucose and fructose. After filtration and concentrating to 82 degrees Brix, the resultant syrup had improved flavor and clarity. However, a more intense maple flavor may be desired. The flavor can be improved by using a more continuous evaporation/concentration system such as a plate heat exchanger with a flash system.

EXAMPLE 5

Flavor Improvements by Blending

To increase the maple flavor profile of the maple syrup at higher Brix, treated syrup was blended with untreated syrup prior to concentration of the syrup as described in Example 3. Four blend ratios have been evaluated: 45:55, 50:50, 55:45, 60:40 (45 degrees Brix treated maple syrup to 55 degrees Brix untreated maple syrup). The concentration to 82 degrees Brix was carried out under vacuum (0.8 bar) and at a lower temperature (60 degrees Celsius). The resultant flavor profile was much improved over product produced in examples 3 and 4. Also, a shelf-life of more than 8 months is attainable with the 55:45 enzyme treated to pure maple syrup blend. Other blend ratios may be possible, for example 20 percent, but this would result in a shelf life of only about three weeks. For extended shelf life, a pure (100 percent) treated syrup could be concentrated as in Example 4, but the flavor and texture would be less desirable.

EXAMPLE 6

Shelf Life of Maple Product at 75. 80, 83 and 87 Degrees Brix

Using a blend of 55:45 enzyme treated to non-enzyme treated syrup, further shelf life evaluations were carried out; evaluating the influence of maple syrup concentration. A blend of 55:45 enzyme treated to non enzyme treated syrup was concentrated using an experimental continuous evaporation system. The system was set-up to concentrate the product to 87 degrees Brix. A portion of this product was then diluted using deionized water to 75, 80 and 83 degrees Brix. Resultant samples are being stored in the dark at room temperature (20 –25 degrees Celsius). Shelf life studies of the four samples (75, 80, 83, 87 degrees Brix) show no visual signs of crystallization.

EXAMPLE 7

Viscosity

The viscosity of the maple syrup was determined at various concentration. A 55:45 enzyme to non enzyme treated syrup blend was concentrated to 87 degrees Brix using an experimental continuous evaporation system. A sample of this product was then diluted to 75, 80 and 83 degrees Brix. The viscosity of the maple syrup was measured at each of the four concentrations (75,80,83,87 degrees Brix) Carri-Med $CLS^2$ 500 Rheometer (TA instruments, New Castle, Del.). A shear rate sweep (0 to 643 reciprocal seconds) was performed on each of the sample using a 2 cm, 4 degree cone and plate geometry. Temperature of the sample was controlled to 25 degrees Celsius. Because of the high viscosity of the samples, all samples were pre-warmed to 80 degrees Celsius prior to testing. Sample were then placed onto the testing apparatus and allowed to cool to the test temperature. The average viscosity of three runs is presented in Table 1.

TABLE 1

| Viscosity of Maple Syrup at Various Concentrations determined at 40 Reciprocal Seconds | |
|---|---|
| Concentration | Viscosity, Pa.s |
| 75 | 1.48 |
| 80 | 11.8 |
| 83 | 61.5 |
| 87 | 487 |

While the invention has been particularly shown and described with a reference to a preferred embodiment, it will be understood by those skilled in the art that various changes in form and detail may be made therein without departing from the spirit and scope of the invention.

I claim:

1. A method for producing a shelf stable, spreadable maple syrup composition which comprises:
   a) adding a sucrose-cleaving enzyme to maple syrup;
   b) incubating the resulting maple syrup solution; and
   c) concentrating the resulting maple syrup solution.

2. The method of claim 1 which additionally comprises the step of removing the sucrose-cleaving enzyme.

3. The method of claim 2, where the sucrose-cleaving enzyme is removed by filtration.

4. The method of any of claims 1, 2 or 3 where the sucrose-cleaving enzyme is invertase.

5. The method of any of claims 1, 2 or 3 where the maple syrup is diluted to 55 degrees Brix prior to the step of adding a sucrose-cleaving enzyme.

6. A method for producing a shelf stable, spreadable maple syrup composition which comprises:
   a) diluting maple syrup to 55 degrees Brix,
   b) adding a sucrose-cleaving enzyme to the maple syrup; where the sucrose-cleaving enzyme is invertase,
   c) incubating the resulting maple syrup solution, and
   d) concentrating the resulting maple syrup solution.

7. The method of claim 6 which comprises the additional step of blending enzyme-treated maple syrup with untreated maple syrup prior to the step of concentrating the resulting maple syrup solution.

8. The method of claim 7 where the ratio of enzyme treated maple syrup to untreated maple syrup is from 45:55 to 60:40 by percentage of sugars present.

9. The method of claim 8 where the ratio of enzyme-treated maple syrup to untreated maple syrup is 55:45 by percentage of sugars present.

10. The method of any of claims 6 to 9, where the resulting maple syrup solution is concentrated to between about 75 degrees Brix and about 90 degrees Brix.

11. The method of any of claims 6 to 9, where the resulting maple syrup solution is concentrated to between 77 and 87 degrees Brix.

12. The method of any of claims 6 to 9, where the resulting maple syrup solution is concentrated to between 82 and 85 degrees Brix.

13. The method of any of claims 6 to 9 , where the resulting maple syrup solution is concentrated to 82 degrees Brix.

14. The method of claim 6 where the resulting maple syrup solution is concentrated under vacuum using low heat of less than 65 degrees Celsius.

15. The shelf stable maple syrup composition made by the method of claim 1, wherein the maple syrup composition is substantially free from crystallization for a period of at least 3 months.

16. The shelf stable maple syrup composition made by the method of any of claims 6 to 9, wherein the maple syrup composition is substantially free from crystallization for a period of at least 3 months.

17. The shelf stable maple syrup composition made by the method of claim 10, wherein the maple syrup composition is substantially free from crystallization for a period of at least 3 months.

18. The shelf stable maple syrup composition made by the method of claim 11, wherein the maple syrup composition is substantially free from crystallization for a period of at least 3 months.

19. The shelf stable maple syrup composition made by the method of claim 12, wherein the maple syrup composition is substantially free from crystallization for a period of at least 3 months.

20. The shelf stable maple syrup composition made by the method of claim 13, wherein the maple syrup composition is substantially free from crystallization for a period of at least 3 months.

21. A shelf stable, spreadable maple syrup composition having a Brix measurement of between about 75 and about 90 degrees, wherein the maple syrup composition is substantially free from crystallization for a period of at least 3 months.

22. A shelf stable, spreadable maple syrup composition having a Brix measurement of between about 77 and about 87 degrees, wherein the maple syrup composition is substantially free from crystallization for a period of at least 3 months.

23. A shelf stable, spreadable maple syrup composition, having a Brix measurement of between about 82 and about 85 degrees, wherein the maple syrup composition is substantially free from crystallization for a period of at least 3 months.

24. A shelf stable, spreadable maple syrup composition, having a Brix measurement of about 82 degrees. wherein the maple syrup composition is substantially free from crystallization for a period of at least 3 months.

25. The method of using the composition of claim 16 as a spread, which comprises spreading the composition on a food product.

26. The method of using the composition of claim 15 as a sweetener which comprises adding the composition to a food product.

27. The method of using the composition of claim 15 as a topping for a food product, which comprises applying the composition to a food product.

28. The method of using the composition of claim 15 as an ingredient in pure maple-based products, which comprises adding the composition to a pure maple-based product during manufacture of the pure maple-based food product.

* * * * *